United States Patent [19]

Schlabach et al.

[11] Patent Number: 4,895,809

[45] Date of Patent: Jan. 23, 1990

[54] IMMOBILIZED ANTIGEN-ANTIBODY DISPLACEMENT PROCESS

[75] Inventors: Timothy D. Schlabach, Pittsburg, Calif.; Fred E. Regnier, West Lafayette, Ind.

[73] Assignee: Varian Associates, Inc., Palo Alto, Calif.

[21] Appl. No.: 569,361

[22] Filed: Jan. 9, 1984

[51] Int. Cl.$^4$ ............... G01N 33/543; G01N 33/558; G01N 22/538; G01N 30/02

[52] U.S. Cl. ................................ 436/518; 436/514; 436/541; 436/546; 436/161; 436/172; 436/177; 436/178; 436/800; 436/807; 436/808; 436/824; 422/68; 422/69; 422/70

[58] Field of Search ............... 436/800, 807, 808, 824, 436/518, 827, 810, 161, 172, 178, 517, 514, 541, 544, 546; 422/70, 61, 68, 69

[56] References Cited

U.S. PATENT DOCUMENTS

| | | | |
|---|---|---|---|
| 4,036,946 | 7/1977 | Kleinerman | 424/8 |
| 4,108,603 | 8/1978 | Regnier et al. | 23/230 B |
| 4,251,360 | 2/1981 | Goldie et al. | 424/1.5 |
| 4,264,327 | 4/1981 | Blum | 23/230 B |
| 4,277,560 | 7/1981 | Gray et al. | 435/7 |
| 4,456,689 | 6/1984 | Witty et al. | 436/500 |

OTHER PUBLICATIONS

Regnier, Science, vol. 222, No. 4621, 245-252, 1983.

Primary Examiner—Robert J. Warden
Assistant Examiner—Jack Spiegel
Attorney, Agent, or Firm—Stanley Z. Cole; Gerald M. Fisher; David Schnapf

[57] ABSTRACT

A method and apparatus for quantitatively analyzing, in a flowing stream, materials in a biological or chemical sample utilizes immobilized antobodies reversibly precharged with fluorescently labeled antigens. The labeled antigens are competitively displaced by unlabeled antigens in the sample, after the sample antigens have been segregated into zones by a chromatographic device, such as the reverse phase high performance liquid chromatograph. Displaced labeled antigens are measured by a fluorescence detector. A plurality of antibody species may be concurrently utilized, thereby allowing quantification of a plurality of antigens from a single sample.

10 Claims, 2 Drawing Sheets

IMMOBILIZED ANTIGEN-ANTIBODY DISPLACEMENT PROCESS

TECHNICAL FIELD

This invention relates to novel methods and apparatus for the chromatographic separation and immunological quantification of biological materials, and, more specifically, to detection and quantification utilizing fluorescently labeled materials.

BACKGROUND ART

Liquid chromatographic techniques are well known in the separation of chemical or biological compounds. Chromatographic separations of biological materials may be accomplished through the use of high performance (or high pressure) liquid chromatography (HPLC), and reverse phase HPLC has been found to be particularly useful. Chromatographic packings are made from small, porous particles with suitable, organic moieties on the surface. They are loaded into a hollow column, and the sample containing the materials to be separated is introduced into the column and allowed to flow through, either by the pull of gravity or by mechanical action, as for example through the use of an associated pump.

Once such biological or chemical materials have been separated into zones, they must be identified. In many instances the compounds must also be quantified. To this end, various techniques have been developed. These include the ultraviolet absorption profile of the column eluate. Associated chart recorders or other devices indicate by a change in the transmission of ultraviolet light through the flow path when detectable species enter the detector. Such a detection system requires a sufficient quantity of materials to provide detectable amounts. In many instances, the small quantities of available samples, difficulties in resolving molecular species of similar size and charge, as well as the presence of large amounts of sample matrix materials with similar bulk properties preclude effective analysis using the general detection scheme indicated above.

Many samples for which detection and identification is desirable are of compounds present in amounts too small to be quantified by conventional procedures. Thus, many other techniques such as those generally characterized by antibody-antigen reactions have been developed.

An immunogen is a chemical or biological substance capable of eliciting production of antibodies when it is introduced into a responding organism. An antigen is a substance that is bound by the antibody. The challenged organism responds via the immunological production of antibodies directed specifically towards the foreign antigen. Once isolated and purified, antibodies capable of binding to a specific given antigen become very useful laboratory reagents. Such antibodies may be tagged with radioactive or fluorescent labels, and an antibody-antigen complex may be formed in a reaction vessel when a given antigen is exposed to such antibodies. The antigen-antibody complexes may be separated from the reaction vessels and indirectly quantified on the basis of the label present in the complex. Enzymes may also be similarly linked to appropriate antibodies and the presence of the enzyme-antibody-antigen complex may be detected by measuring the reaction of the enzyme with a given substrate.

Alternatively, such labels may be coupled to antigen molecules, thereby giving rise to competitive binding assays to determine the presence and quantity of a given antigen based upon the competition for antibody binding sits between a known amount of labeled antigen and an unknown amount of unlabeled antigen present in a particular chemical or biological sample material. Such techniques are well known in the art.

It is also known in the art to attach antibodies to a solid support, thereby forming a testing material that can specifically bind to labeled or unlabeled antigens in a chemical or biological sample, which presence may be subsequently detected by the monitoring of fluorescent or radioactive labels, for example. These types of assays are generally discussed in U.S. Pat. Nos. 4,273,756, 4,272,505, 4,272,504, and 4,277,560.

The '560 patent discloses the use of immobilized antibodies that are saturated with enzyme-antigen complexes to reversibly bind to the immobilized antibody. The unlabeled antigen in a given sample is injected into a stream that flows directly into a first stage packed column containing the immobilized antibody, and a competitive equilibrium process takes place between the antigen-enzyme complex bound to the antibody and the unlabeled antigen of the sample as it flows past the antibodies immobilized on the substrate. Thus, a given quantity of labeled antigen is released into the flowing stream, to be measured downstream after reaction with a second, or detection, stage, such as a suitable enzyme substrate. A measurable reaction product may be quantitatively determined, and the concentration of the unlabeled antigen in the original sample may also be determined, such concentration being related to the amount of enzyme activity detect by the second stage. The '560 patent teaches the use of a first stage device having antibodies specific for only a single antigen. Thus, this technique is useful only for the quantification of antigens which have previously been identified, and a different immobilized antibody stage would be required for the quantification of a second antigen.

The '505 patent discloses a thyroid hormone assay involving competitive binding of labeled antigens with the same antigen from a biological fluid sample. The amount of thyroid hormone in the sample may be calculated from the fluorescence measurement of the sample as compared with a standardized data table from the assay.

No related method or apparatus is known that allows the convenient quantification of a plurality of antigens from a given biological sample using a post-chromatographic separation antibody-antigen competitive binding component.

DISCLOSURE OF THE INVENTION

It is accordingly one object of the present invention to provide a novel immobilized antibody detection stage useful for the quantification of a plurality of antigens from a given biological or chemical fluid sample.

A further object of the present invention is to provide such a detection system in which immobilized antibodies of several specificities may be used to quantitatively bind and detect a plurality of antigens.

A still further object of the present invention is directed toward utilizing fluorescently labeled antigens in the detection system, that may be competitively displaced by unlabeled antigens from the sample fluid.

It is a further object of the present invention to provide a detection system that may be conveniently and easily coupled to a conventional chromatographic separation process such as high performance liquid chromatography, HPLC, particularly reverse phase HPLC.

Other objects and advantages of the present invention will become apparent as the description thereof proceeds.

In satisfaction of the foregoing objects and advantages, there is provided by the present invention, a method for quantitatively determining the amount of a plurality of antigens in a biological sample. This method first requires the segregation of the sample antigens into distinct zones such as by high performance liquid or other column liquid chromatographic techniques. Subsequently, these antigen zones are allowed to pass through a post segregation detection system. This detection system includes a competitive binding component and a detector. The binding component includes immobilized antibodies specifically and reversibly coupled to various of the sample antigens, in which the antibody-antigen complexes include fluorescent labels attached to the antigens. Thus, as the antigen zones pass through the post-chromatographic detection system, the labeled antigens are competitively displaced by corresponding sample antigens, and enter the detector in a stream of carrier fluid flowing through the system. In the detector, the amount of labeled antigen may be quantified by standard fluorescence measurement techniques. From this measurement, the quantity of unlabeled antigen in the sample may be determined.

BRIEF DESCRIPTION OF THE DRAWINGS

The objects, features, and advantages of the present invention will be better understood from the following detailed description when considered in conjunction with the accompanying drawings in which.

BEST MODE FOR CARRYING OUT THE INVENTION

As indicated above, one aspect of the present invention is concerned with a post-chromatographic competitive binding component utilizing immobilized antibodies. The terms "chromatograph" and "chromatography" refer generally to both conventional, gravity-fed columns and to pressurized systems such as HPLC.

Figure 1:
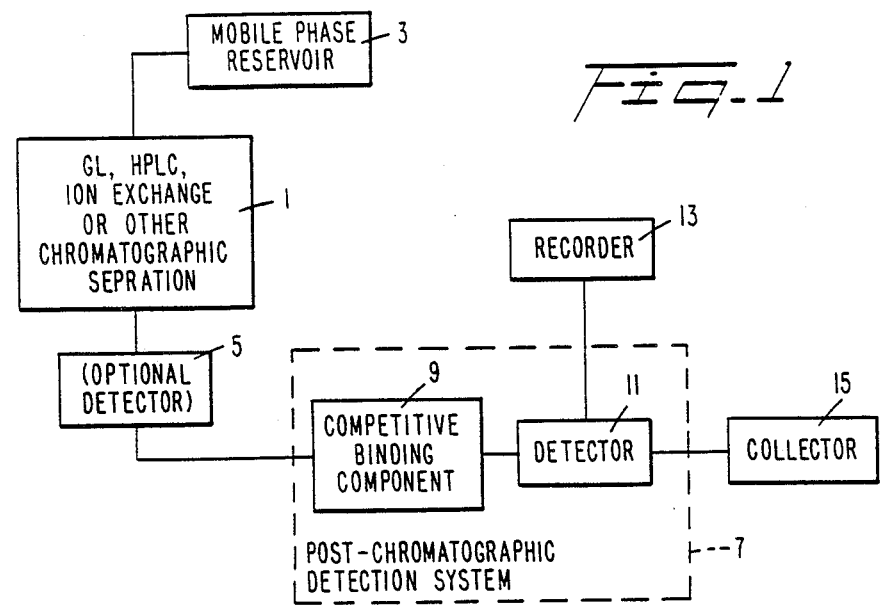
FIG. 1 is a schematic block diagram of the separation and immunological detection system of the present invention.

FIG. 1 illustrates a schematic block diagram of the antigen chromatographic separation and post-chromatographic detection system of the present invention. A sample containing a plurality of different antigens is introduced into a conventional chromatographic separation device 1, such as a high performance liquid chromatograph. A reservoir 3 of appropriate eluent provides a carrier medium to elute the sample through the column. A pressurizing system, such as a reciprocating pump or a motorized syringe pump, is necessary with the HPLC system.

After the sample has eluted from chromatographic separation device 1, an optional detector 5 may be used for activation of the subsequent elements of the system. For example, the eluent flow may be diverted into a collection reservoir until detector 5 shows the presence of eluate.

The continuous flow of eluent carrying the eluate next enters a post-chromatographic detection system 7 that includes a competitive binding component 9 and a detector 11. Binding component 9 contains immobilized antibodies, and will be discussed in detail below; however, generally speaking, unlabeled antigens from the sample material competitively displace fluorescently labeled antigens previously reversibly bound to the immobilized antibodies within the component. Detector 11 monitors the released labeled product of competitive binding in binding component 9, and is associated with a recorder (or data storage device) 13 and an eluent collector 15.

Figure 2:
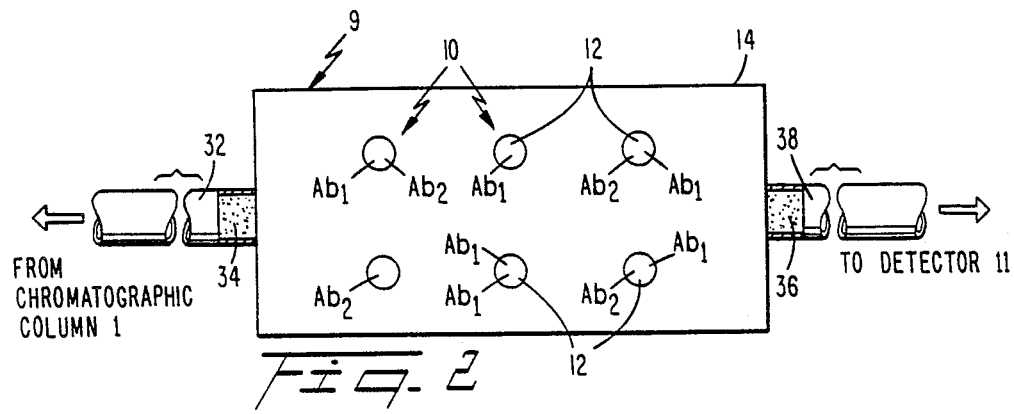
FIG. 2 is a partial view of the competitive binding component of the post-chromatographic detection system of the present invention in its initial state.

Competitive binding component 9 includes a suitable vessel 14, as shown in FIG. 2, containing a large number of glass or polymeric beads 12 to which antibodies, generally indicated at 10, have been immobilized. A conduit 32 connects chromatographic device 1 to binding component 9, and contains a frit, or filter, 34 proximate to binding component 9. Component 9 is connected in turn to detector 11 via a second conduit 38 having a frit 36.

Antibodies may be immobilized, for example, on nonporous glass beads, by several methods. For example, propylamine could be attached first to the glass surface by reacting amino-propyltrimethoxysilane with the glass beads according to Jacobson et al, *Biochem. Biophys. Acta,* 506, 81, 1978. Antibody can be subsequently attached to the bound propylamine through amino groups in the antibody protein, specifically, IgG immunoglobulins. This attachment can be accomplished with a bifunctional imidoester, such as dimethyl adipimidate, which has been used to immobilize enzymes on aminoethyl cellulose according to Campbell, *Biochem. Biophys, Acta,* 403, 79, 1975. Antibody could alternatively be coupled to the bound propylamine with a mixed anhydride, such as N-ethoxycarbonyl-2-ethoxy-1,2-dihydroquinoline. This reagen activates protein carboxyl groups (see Sandaram, *Biochem. Biophys, Res. Comm.,* 61, 717, 1974) so that they form amide bonds with primary amines. See also U.S. Pat. No. 4,273,756.

The immobilized antibodies in vessel 14 would next be saturated with appropriate corresponding labeled antigens to which the particular antibody species are specifically directed. This saturation step may be completed prior to inserting binding component 9 into the system.

Figure 3:
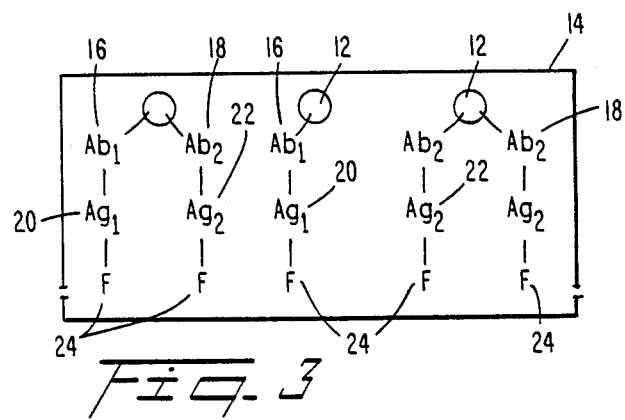
FIG. 3 is the competitive binding component of FIG. 2 after the component has been saturated with labeled antigens prior to use.

FIG. 3 generally represents antibodies 10 reversibly bound to fluorescently labeled antigens. A first species of antibody 16 is represented by "$Ab_1$" and a second species of antibody 18 is represented by "$Ab_2$". The antigen 20 corresponding to antibody 16 is represented by "$Ag_1$", and the antigen 22 corresponding to antibody 18 is "$Ag_2$". A fluorogenic or fluorescent marker (F) 24 is shown attached to the antigens 20 and 22, bound in turn to their corresponding antibodies, as represented by "Ag$_1$-F" or "Ag$_2$-F". Although only two different antibodies are shown coupled to the beads 12 of the present invention, it will be apparent that more than two such antibodies may be utilized in the competitive binding component of the present invention, subject, however, to limitations imposed on the system by factors such as non-specific binding, or the potential cross reactivities of the antibody species utilized.

In use, the column eluent would be passed through the competitive binding component for a short period such as approximately ½ hour prior to introducing the sample into the chromatographic system. This allows the removal of non-covalently or weakly held reagents, such as loosely bound label or labeled antigens.

Samples containing appropriate antigens would first be separated chromatographically into segregated zones by passage through a liquid chromatographic column, for example, typically a reverse phase column. Antigens eluting from the column would next enter the competitive binding component of the post-chromatographic detection system. There the unlabeled sample antigens would displace the corresponding labeled antigen held by the immobilized antibody, through a competitive binding process.

Figures 4, 5, 6:
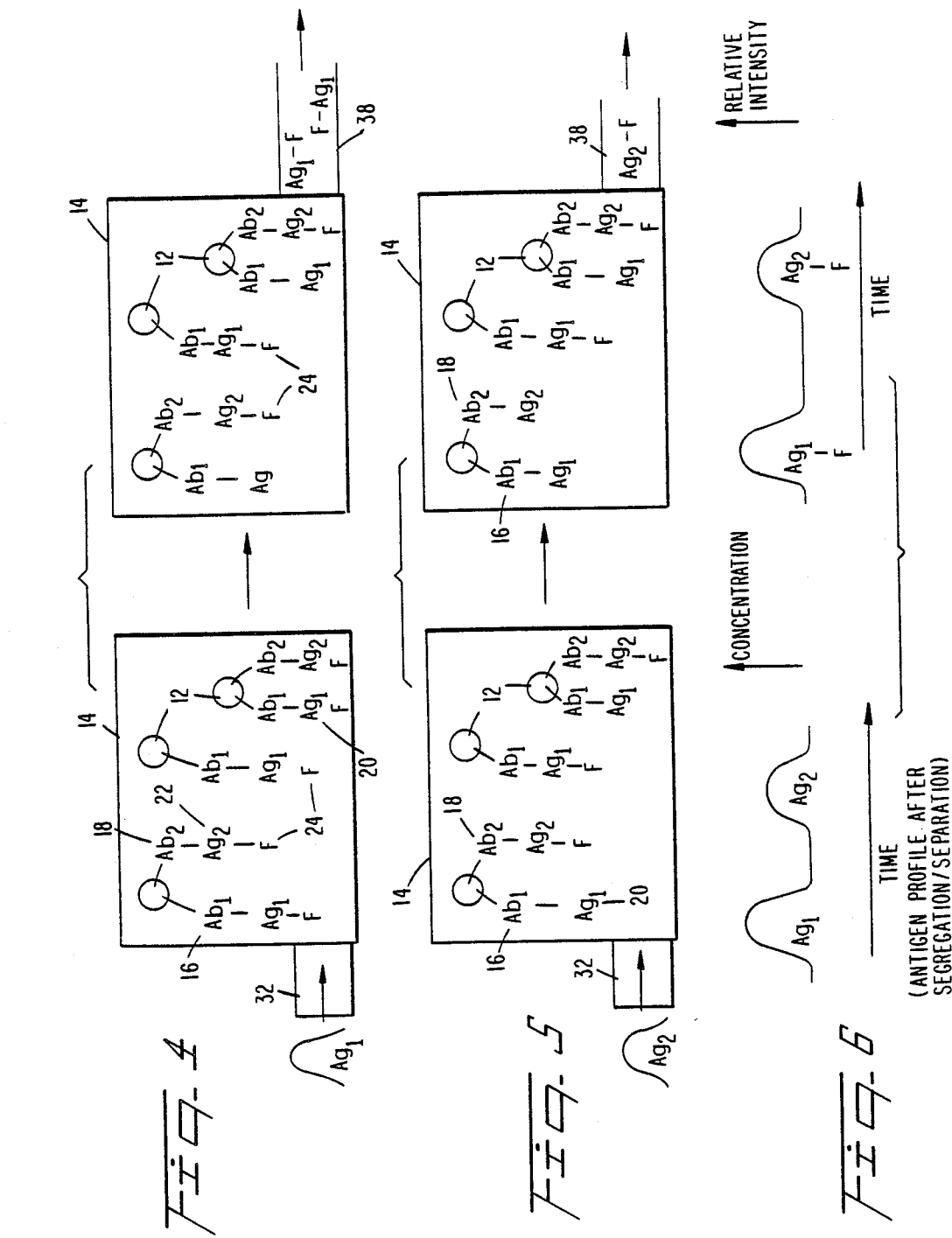
FIG. 4 is the competitive binding component of the present invention representing the passage of a first antigen zone through the component.
FIG. 5 shows the competitive binding component while a second antigen zone is passing through it.
FIG. 6 shows the comparison of the antigen profile after its segregation by the chromatography stage and the detection profile of the corresponding fluorescently labeled antigen peaks passing through the detector after the competitive binding step has been completed.

As illustrated in FIG. 4, a fluorescently tagged antigen, when displaced, would either exit the competitive binding component 9 along with the eluent continuously flowing therethrough or displace another tagged antigen. Thus, the antigen zone representing Ag$_1$ would displace only those fluorescently tagged Ag$_1$ molecule complexes attached to Ab$_1$ antibodies. Eventually, one fluorescently labeled Ag$_1$ leaves the vessel for every sample Ag$_1$ retained by the immobilized antibodies in competitive binding component 9. Note that the Ag$_1$ zone does not affect Ab$_2$-Ag$_2$-F complexes.

As shown in FIG. 5, when the Ag$_2$ zone enters binding component 9, a similar process takes place between this unlabeled antigen and the fluorescently labeled Ag$_2$ complexes attached to the Ab$_2$ antibodies. In turn, the fluorescently labeled antigens would be detected with a conventional, liquid chromatographic fluorescence detector, for example, and the detector response will be directly proportional to the unlabeled antigen concentration in the sample.

FIG. 6 illustrates the correspondency between the chromatographic antigen elution profile and the fluorescent intensity of labeled antigen zones detected after being displaced from the competitive binding component by unlabeled sample antigens.

Certain advantages stem from the use of the competitive binding system of the present invention. Due to the sensitivity of the detection system and the presence of labeled antibody-antigen complexes in excess, a given charged competitive binding component may be reused for several samples. Additionally, because the antibodies are immobilized, they may be re-charged with labeled antigen, to regenerate the competitive binding component after sufficient sample preparations have run through the system to reduce the total amount of reversibly bound fluorescently labeled antigen. Furthermore, multiple antibody species, with varying specificities, may be immobilized simultaneously so that different types of sample antigens can be detected by the system. A major advantage of this system is that it is able to perform the competitive binding assay in a flowing stream. This type of system would be particularly useful in identifying individual polypeptides and proteins in biological samples. A further advantage is the elimination of the incubation periods required by previous competitive binding techniques.

Contemplated equivalents of the competitive binding component of the present invention include the use of other specific binding agents, as for example, hormone receptors, to which fluorescently labeled hormones may be reversibly coupled and that would be displaced into the flowing stream for detection by the action of a sample containing the same but unlabeled hormone.

Some fluorescently labeled antigens may be obtained commercially from various supply houses. Others can be simply prepared by reacting dansyl chloride with a suitable antigen at a pH of 7–8, as is known in the art. An appropriate fluorescent tag may be rhodamine (red fluorescence) or fluorescent (green fluorescence). Thus, qualitative analyses may be performed when various fluorescent labels are coupled to the reversibly bound antigens. A detector system with multiple detection channels, such as two fluorescence detectors in series, can perform multicomponent analysis of poorly segregated, antigen zones. The post-chromatography competitive binding component may be produced in the form of interchangeable cartridges that may be substituted into the chromatography-competitive binding-detection system depending on the particular antigen or antigen mixture to be quantified.

This system is useful in the selective quantification of certain antigenic substances that may be bound by specific antibodies. The system is also highly useful for detection with those samples in which the antigen may be present in amounts too small for accurate quantification by other means. Purification of selected antigenic macromolecules may also be an advantage of this system.

From the foregoing description, one skilled in the art can easily ascertain the essential characteristics of this invention, and without departing from the spirit and scope thereof, can make various changes and modifications of the invention to adapt it to various usages and conditions. The following preferred specific embodiment is, therefore, to be construed as merely illustrative and not limitative of the disclosure in any way whatsoever. In the example and throughout the specification, parts are by weight unless otherwise indicated.

EXAMPLE

A competitive binding component of the present invention directed towards the quantification of human thyroid hormone is prepared as follows. Anti-thyroid hormone IgG may be obtained commercially or is prepared by immunizing adult rabbits with immunogenic dosages of human thyroid hormone and adjuvant, a procedure well known in the art. This antibody is bound to glass beads of approximately 50 microns in diameter, also commercially available, by first treating the glass beads with aminopropyltrimethoxysilane to form propylamine, and then subsequently attaching the antibody through the use of a bifunctional imidoester, such as dimethyl adipimidate. The beads are then packed into an appropriately unreactive column, such as of pyrex.

The antibodies so immobilized are then exposed to a solution containing fluorescently tagged human thyroid hormone, thereby forming reversibly bound antibody-antigen complexes.

The post-column competitive binding component thus formed is placed in line to receive a continuous flow from a liquid chromatographic column. The column eluent is allowed to run through the post-column components for 30 to 60 minutes to remove any weakly or non-covalently bound fluorescently labeled antigen.

Following this washing period, introduce a 0.10 ml sample containing an unknown quantity of human thyroid hormone to the liquid chromatographic column. Allow the sample to pass through the column and the eluent to enter the inlet connecting tube to the post-column competitive binding component. As the thyroid hormone and other materials pass through the liquid chromatographic column, they are separated into various zones depending on relative size and absorptive properties. When the particular zone containing the human thyroid hormone enters the competitive binding component, antigen molecules within this zone will displace fluorescently labeled thyroid antigen molecules reversibly bound to the antibodies present in this component. This generates a corresponding peak of fluorescently labeled antigen as displaced into the flowing stream of eluent that next enters the fluorescence detector. The measured quantity of fluorescence may be compared for a given antigen sample to a standard table previously generated for human thyroid hormone in this system. This provides a quantitative measurement of the thyroid hormone present in the initial sample.

What is claimed is:

1. A method for quantitatively determining the amount of a plurality of antigens in a biological sample, comprising the steps of:
   (a) segregating the sample antigens into a plurality of distinct zones by high performance or other liquid chromatographic techniques; and
   (b) allowing said segregated antigen zones to pass through a post-segregation detection system including a competitive binding component and a detector, said competitive binding component including
      (i) immobilized antibodies of a plurality of distinct species effective to specifically and reversibly couple to particular sample antigens, and
      (ii) fluorescently labeled antigens corresponding to the sample antigens that have specifically and reversibly coupled to the corresponding immobilized antibodies,
   such that as said antigen zones pass through said detection system, said labeled antigens are competitively displaced by corresponding sample antigens and enter said detector
   (c) detecting the amount of displaced fluorescence-labeled antigen, said detected amount corresponding quantitatively to a given sample antigen zone.

2. The method of claim 1 wherein the segregation step is performed by a liquid chromatographic device wherein the sample antigens are introduced into a column in which a carrier fluid is used to differentially move said sample antigens along a tube packed with material having varying affinity with said antigens.

3. The method of claim 2 wherein said chromatographic technique is a high performance liquid chromatography, and (said column is coupled to said competitive binding component) to allow a continuous flow of eluent including said antigen zones to pass through said column into said competitive binding component.

4. The method of claim 3 wherein said immobilized antibodies represent a plurality of immunological specificities, and are preselected to correspond to a plurality of known antigens of the sample to be applied to said liquid chromatograph.

5. The method of claim 4 wherein said antigens are segregated by reverse phase, high performance liquid chromatography.

6. The method of claim 1, wherein the segregation step is performed by steric exclusion or ion-exchange chromatography.

7. The method of claim 6, wherein said segregation step is coupled to said competitive binding component to allow a continuous flow of eluent including said antigen zones to pass through said segregation step into said competitive binding component.

8. The method of claim 7, wherein said immobilized antibodies represent a plurality of immunological specificities, and are preselected to correspond to a plurality of known antigens of the sample to be applied to said liquid chromatograph.

9. A device for quantitatively determining the amount of a plurality of antigens in a biological sample, comprising:
   (a) a high performance liquid chromatographic column;
   (b) a competitive binding component including
      (i) immobilized antibodies of a plurality of distinct species effective to specifically and reversibly couple to the sample antigens, and
      (ii) fluorescently labeled antigens corresponding to the sample antigens that are specifically and reversibly coupled to corresponding said immobilized antibodies,
   said column and said competitive binding component coupled to allow a continuous flow of eluent to pass from said column into said binding component; and
   (c) a detector effective to quantitatively determine the amount of fluorescently labeled antigen displaced from said competitive binding component by the passage of unlabeled sample antigen through said binding component, said detector being coupled to said competitive binding component to allow a continuous flow of said eluent to pass from said competitive binding component to said detector.

10. The device claim 9, further including
   (d) a recorder coupled with said detector for recording the amount of fluorescently labeled antigen displaced from said competitive binding component and detected by said detector; and
   (e) an eluent collector coupled with said detector.

* * * * *